(12) United States Patent
Hasbun

(10) Patent No.: US 8,894,585 B2
(45) Date of Patent: Nov. 25, 2014

(54) PORTABLE DIAGNOSTIC INSTRUMENT AND A METHOD FOR ITS USE

(76) Inventor: William M. Hasbun, Mount Laurel, NJ (US)

( * ) Notice: Subject to any disclaimer, the term of this patent is extended or adjusted under 35 U.S.C. 154(b) by 615 days.

(21) Appl. No.: 12/651,510

(22) Filed: Jan. 4, 2010

(65) Prior Publication Data

US 2011/0166473 A1 Jul. 7, 2011

(51) Int. Cl.
*A61B 5/00* (2006.01)
*A61B 5/12* (2006.01)

(52) U.S. Cl.
CPC .............. *A61B 5/12* (2013.01); *A61B 5/0051* (2013.01); *A61B 2560/0431* (2013.01)
USPC ............................ 600/552; 600/301; 600/559

(58) Field of Classification Search
CPC ................................ A61B 5/0051; A61B 5/12
USPC .................................. 600/552, 553, 557, 559
See application file for complete search history.

(56) References Cited

U.S. PATENT DOCUMENTS

| | | | |
|---|---|---|---|
| 1,634,373 A | 7/1927 | Mann | |
| 5,193,528 A | 3/1993 | Iwamoto | |
| 5,522,386 A * | 6/1996 | Lerner | 600/547 |
| 5,746,205 A * | 5/1998 | Virsu et al. | 600/544 |
| 5,806,522 A * | 9/1998 | Katims | 600/554 |
| 7,097,622 B2 * | 8/2006 | Bleustein et al. | 600/555 |
| 7,370,533 B2 | 5/2008 | Davis | |
| 7,892,180 B2 * | 2/2011 | Epley | 600/559 |
| 7,938,784 B2 * | 5/2011 | Boslough et al. | 600/553 |
| 2002/0165013 A1 * | 11/2002 | Bright et al. | 455/567 |
| 2004/0186390 A1 * | 9/2004 | Ross et al. | 600/532 |
| 2004/0212342 A1 * | 10/2004 | Batson | 320/107 |
| 2005/0070334 A1 * | 3/2005 | Ono et al. | 455/566 |
| 2005/0070812 A1 * | 3/2005 | Donofrio | 600/552 |
| 2005/0170818 A1 * | 8/2005 | Netanel et al. | 455/415 |
| 2006/0084885 A1 * | 4/2006 | Reydel | 600/564 |
| 2006/0202859 A1 * | 9/2006 | Mastrototaro et al. | 340/870.07 |
| 2006/0220881 A1 * | 10/2006 | Al-Ali et al. | 340/573.1 |
| 2007/0106169 A1 * | 5/2007 | Fadem | 600/544 |
| 2009/0303073 A1 * | 12/2009 | Gilling et al. | 340/815.45 |
| 2010/0106049 A1 * | 4/2010 | Boslough et al. | 600/553 |
| 2011/0066082 A1 * | 3/2011 | Duffy | 600/595 |
| 2011/0112431 A1 * | 5/2011 | Golosarsky et al. | 600/552 |

* cited by examiner

*Primary Examiner* — Max Hindenburg
*Assistant Examiner* — Michael C Stout
(74) *Attorney, Agent, or Firm* — Muskin & Farmer, LLC; Shawn R. Farmer

(57) ABSTRACT

A portable diagnostic instrument for use by medical professionals. The portable diagnostic instrument can comprise a control unit that can maintain the frequency of sound or vibration produced by the device constant, even when battery power is reduced. The control unit can also comprise a warning unit to provide information about remaining battery life to the user. Furthermore, the portable diagnostic instrument can comprise a unit capable of producing vibration and a unit capable of producing sound at differing frequencies. The device can produce both the sound and vibration at the same time or each can be operated individually. Moreover, the device is capable of being attached to other medical equipment that is carried by a medical professional or can be easily kept in a pocket, so that it is readily available when needed.

13 Claims, 4 Drawing Sheets

PORTABLE DIAGNOSTIC INSTRUMENT AND A METHOD FOR ITS USE

FIELD OF THE INVENTION

This device relates to portable diagnostic equipment for use by medical professionals. More particularly it relates to a portable diagnostic instrument that is capable of generating auditory sounds and vibrations controlled by the user. The portable diagnostic instrument provides the medical professional with the ability to test the hearing and nervous system responses of a patient with a single tool.

BACKGROUND

Portable medical diagnostic equipment can be carried by a doctor or by other medical personnel to provide quick access when needed to examine a patient. Additionally, such devices are generally kept in a pocket or attached to other standard equipment, so that they do not get misplaced and are available whenever needed. These devices must be capable of assisting a medical professional when testing the hearing and nervous system capabilities of a particular patient. These devices must also be reliable. It is an advantage of these devices to be capable of providing more than one function, such as that of an auditory testing device as well as providing tactile stimulation for testing nervous system reactions. Therefore, it is beneficial if such devices can be capable of housing both tools in one piece of equipment, which can be easily transported and readily accessible to medical professionals. It can also be beneficial if such devices contain a self-contained power source, which can provide a sufficient amount of power and be controlled and accurately provide the correct amplitude and frequency of sound waves to properly examine the patient. Additionally, it is beneficial if such devices can provide an indicator informing the user when power is getting low, before the device ceases to operate correctly.

Davis U.S. Pat. No. 7,370,533, describes a "Portable Audiometer Enclosed within a Patient Response Mechanism Housing." As with the present device, the Davis invention describes a portable diagnostic device that generates tones for the purpose of assessing the hearing capacity of an individual. However, the Davis invention, while capable of determining the hearing capacity of a person, does so through a complicated method and is not conducive to making a quick determination as to whether a patient has impaired hearing. Additionally, this device does not provide any other medical assessment tools other than the audiometer. Furthermore, the patented device does not comprise a warning that the battery power is getting low or that the tonal generating features of the instruments will be useless in the near future.

Mann U.S. Pat. No. 1,634,373, existing in the prior art, describes an "Electronic Therapeutic Device." The Mann patent describes a device for use in the medical profession, which provides tactile stimulation to a patient. The device can provide vibration, heat and eddy currents, which are used to strengthen and build human tissue. This patent discusses the use of vibration to stimulate the tactile receptors of a person. However, the Mann patent is used to provide stimulation for a long period of time, so that it can strengthen a particular area of the body. It would be impracticable to use this device as a diagnostic tool to determine the neurological responsiveness of a patient because it has a large surface area and cannot be used to create a response to a small area of stimulation. Additionally, this device does not provide any other diagnostic tools that would help a medical professional in determining other aspects of a patient's health. Furthermore, the device disclosed in the Mann patent uses a corded power source and is not easily portable.

There are other patents that disclose portable medical vibratory tactile stimulation devices, which are powered through the use of batteries, such as Iwamoto U.S. Pat. No. 5,193,582 for a "hand-held vibratory massager." This invention uses vibration to massage the skin. However, it is designed to allow a person to massage hard to reach areas such as his own back. This design in not easily used by a medical professional to stimulate the skin of a patient to observe the neurological response. Additionally, the portion of this device that supplies vibration to a portion of the body has a large surface area. This large surface area cannot be used with certain medical diagnostic functions, such as the Babinski Reflex Test. Moreover, this device does not provide any indication as to the remaining battery power nor does it provide any other medical benefit other than vibration of the skin.

What is needed is a portable diagnostic instrument comprising an audiometer that can provide tones in a range of frequencies and can also be used for other medical diagnosis. The device must be able to produce sounds at an accurate pitch and amplitude, even when battery power is reduced. Additionally, a warning unit is needed to provide information about the remaining battery life to the user. Furthermore, a portable diagnostic device is needed that comprises a vibratory unit, which can be used to assess the sensory perception and neurological function of a patient.

SUMMARY OF THE INVENTION

It is an aspect of the present device to provide an improved portable diagnostic instrument capable of testing multiple aspects of human health.

The above aspect can be obtained by a portable diagnostic instrument comprising an auditory unit capable of producing sounds in a variety of frequencies, a vibratory unit capable of producing vibration, a control unit to control monitor the auditory unit and the vibratory unit, and a warning unit to control and monitor the instruments power supply.

The above aspect can also be obtained by a method for using a portable diagnostic instrument, the method comprising providing a unit combining a vibratory unit and an auditory unit, turning on the vibratory unit, placing the vibratory unit, against a patient's skin and observing the reaction produced by the contact, turning on the audible unit to produce sound, varying the frequency of the sound produced by the device, and observing which frequencies are perceptible by the patient.

These together with other aspects and advantages which will be subsequently apparent, reside in the details of construction and operation as more fully hereinafter described and claimed, reference being had to the accompanying drawings forming a part thereof, wherein like numerals refer to like parts throughout.

BRIEF DESCRIPTION OF THE DRAWINGS

Further features and advantages of the present device, as well as the structure and operation of various embodiments of the present device, will become apparent and more readily appreciated from the following description of the preferred embodiments, taken in conjunction with the accompanying drawings of which.

DETAILED DESCRIPTION

Figure 1:
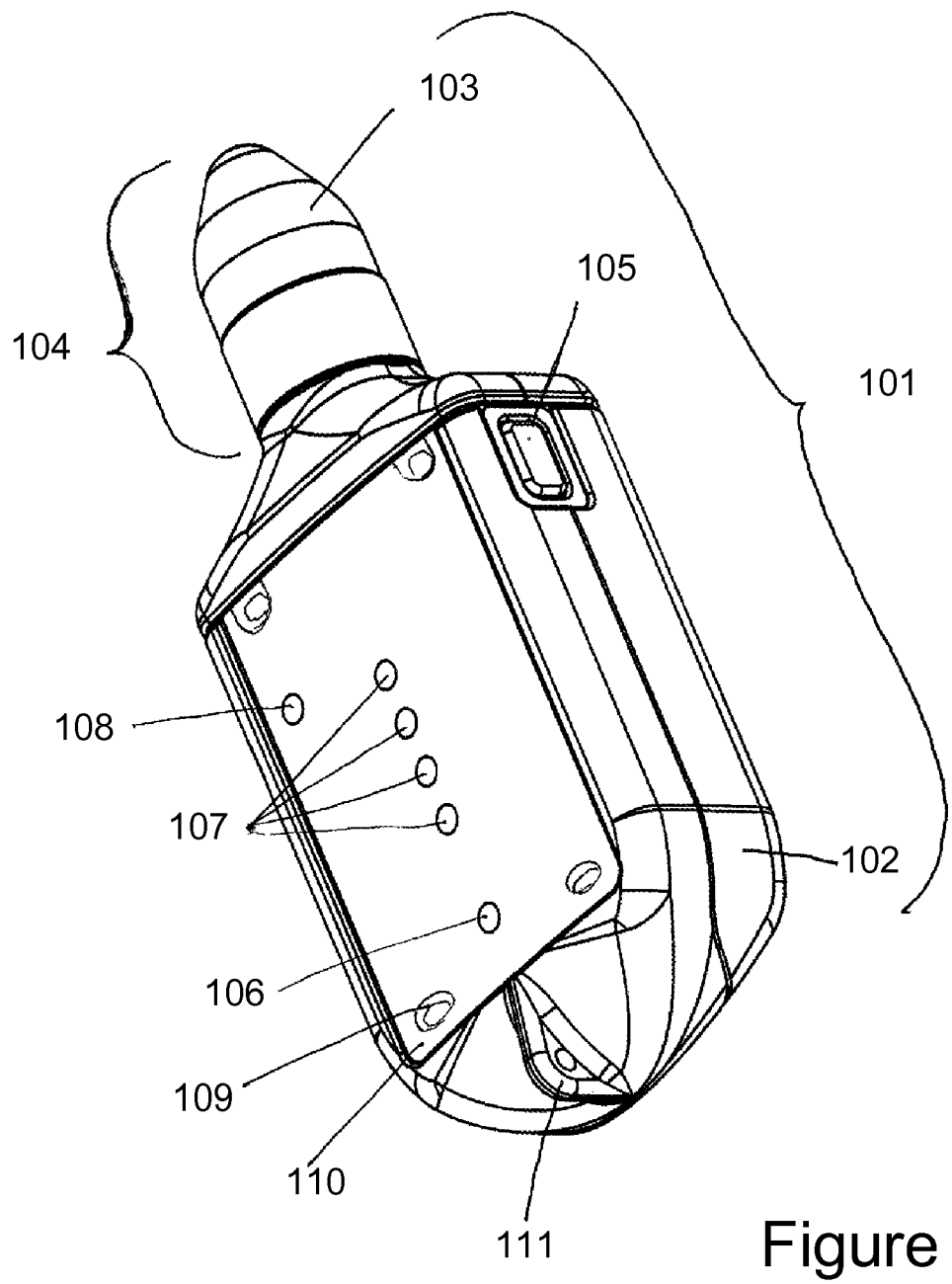
FIG. 1 is a perspective top view of a portable diagnostic instrument according to an embodiment.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Reference will now be made in detail to the presently preferred embodiments of the invention, examples of which are illustrated in the accompanying drawings, wherein like reference numerals refer to like elements throughout.

The portable diagnostic instrument is a small device that can be carried in a pocket or attached to a keychain. Despite its size, the portable diagnostic instrument can perform two very important functions, which are often necessary to properly diagnose a patient.

First, it can test an individual's sensory perception by use of a vibratory unit which can produce vibrations of various frequencies. The tip of the vibrating unit can placed against various parts of the human body, including the shin of a patient being examined. A patient's capacity for sensing this vibration can be an indication of his or her sensory perception.

Second, the portable diagnostic instrument can be used to test a patient's hearing. Various frequencies of sound can be produced by an auditory unit while the instrument can be held near a patient's ear in order to determine his or her ability to hear. The instrument can also be used to test both the individual's sensory perception and his or her hearing simultaneously.

FIG. 1 is a top perspective view of a portable diagnostic instrument 101 according to an embodiment.

Referring to FIG. 1, the portable diagnostic instrument 101 can comprise a housing 102, which can provide protection to the device 101 from impact or other environmental elements. Along with the housing 102, a cap 103 can cover the vibratory mechanism 104 to protect this feature from similar threats.

The housing 102 can comprise a switch 105 that can either activate or deactivate the vibratory function of the device. One or more sides of the device 101 can comprise several indicator lights 106, 107 and 108. These lights can be light emitting diodes or similar light producing devices known on the art. One or more of these indicator lights 106 can comprise part of a warning unit, which can inform the user as to the amount of power that remains in a rechargeable battery or similar power storing device. This battery power indicator 106 can be capable of illuminating in three different colors, being lit a first color to indicate a full battery charge, as second color to indicate partial battery charge remaining and a third color to indicate low battery power remaining.

A second set of indicator lights 107 can be used to indicate the frequency of the sound or vibration that is being produced by the device 101. Only the light indicating the frequency being produced at that particular time can be lit.

The third indicator light 108 can be located on the housing 102 and can display the charging status of the battery. This indicator 108 can indicate when the device 101 is charging, unable to charge or fully charged, by flashing or being illuminated in different colors corresponding to the current charging status.

The housing 102 can comprise one or more pieces which can be secured to the internal components and to itself through the use of screws 109 or similar fastening devices, which can be inserted into holes 110 that are formed to accept the screws 109. As an additional portability feature, the device can include a key ring hole 111 on the housing at the end opposite of the vibratory feature 104. The key ring hole 111 can be used to attach the device 101 to a variety of things commonly kept on the body of a medical professional, such as keys, so that the device 101 can be easily accessible for use on a patient.

Figure 2:
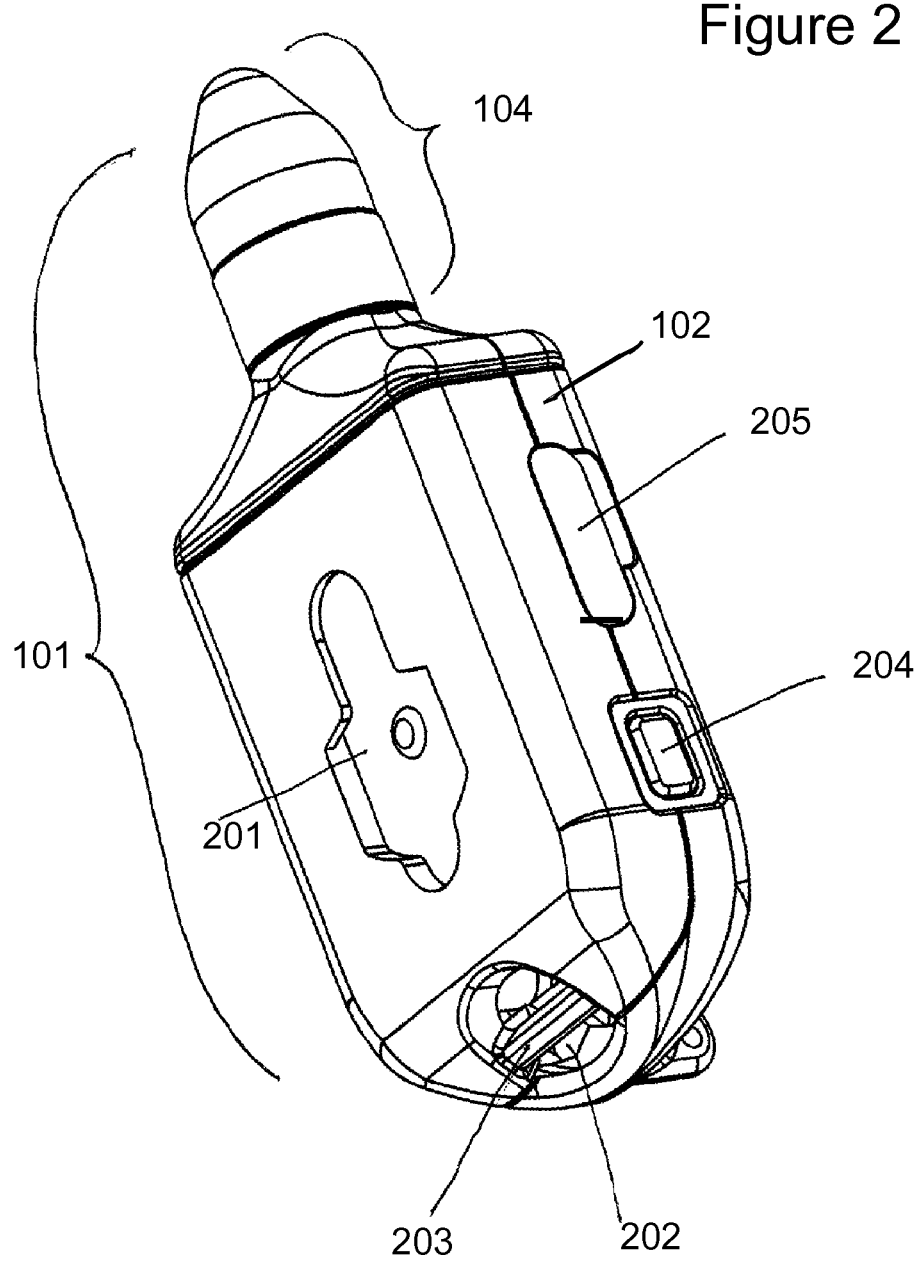
FIG. 2 is a perspective bottom view of a portable diagnostic instrument according to an embodiment.

FIG. 2 is a bottom perspective view of a portable diagnostic instrument 101 according to an embodiment.

The housing 102 can have a slot 201 on the bottom side of the device for attaching additional accessories. The slot 201 can be located in the middle of the flat portion of the bottom of the housing 102. On the end of the device 101 opposite of the vibratory unit 104 can be the location of the speaker 202. These sounds can closely match those created by standard tuning forks currently used to conduct such hearing tests. The speaker 202 can be used to produce sounds of varying audio frequencies, which can be used to test the ability of a patient to hear. The speaker 202 can be covered by a bar 203, which can be used to protect the speaker 202 from being damaged.

Along one side of the device 101 can be located a switch 204 that can turn the sound on or off. A charging port 205 can also be located on this side of the device. The charging port 205 can be a micro USB or similar port that is capable of providing electricity to the battery (not shown).

Figure 3:
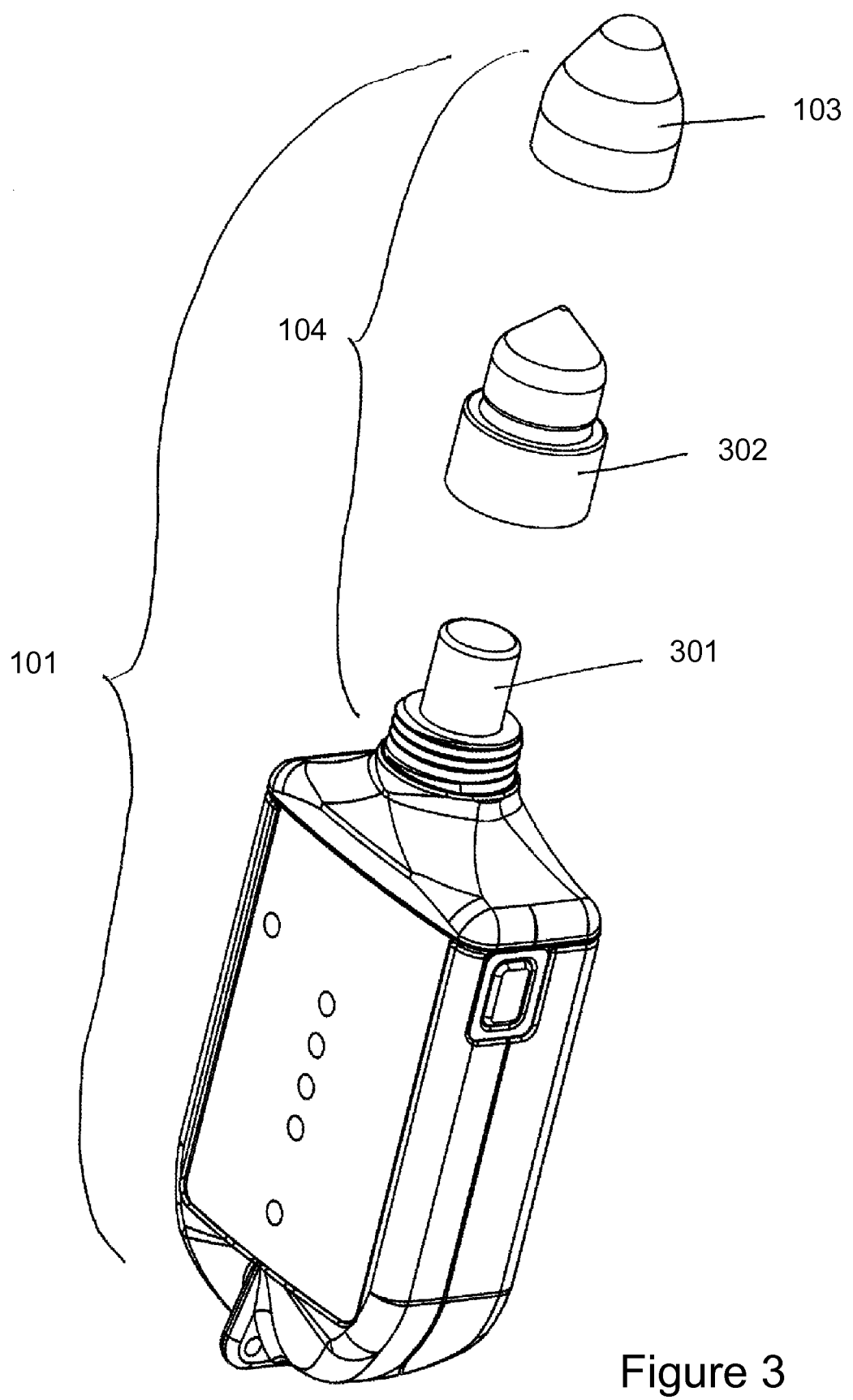
FIG. 3 is a partially exploded perspective view of a vibratory unit of a portable diagnostic instrument according to an embodiment.

FIG. 3 is a partially exploded perspective view of a vibratory unit 104 of a portable diagnostic instrument 101 according to an embodiment;

The vibratory unit 104 can comprise a vibratory post 301, a first cap 302 and second cap 303. The vibratory post 301 can be located at the end of the device 101 and can provide the vibration necessary for diagnostic testing of a patient's tactile perception and neurological function. A first cap 302 can be located on the vibratory post 301. This first cap 302 can be made of metal or other material and can be used for testing the Babinski reflex. The first cap 302 can focus the vibratory energy onto a small surface area to increase its effect. This first cap 302 can also be screwed onto the vibratory post 301 and can provide protection for the vibratory post 301. A second cap 103 can be secured over the first cap 302. The second cap 103 can provide protection from dirt and moisture for the entire vibratory unit 104. This second protective cap 103 can be made of a plastic or other suitable material.

Figure 4:
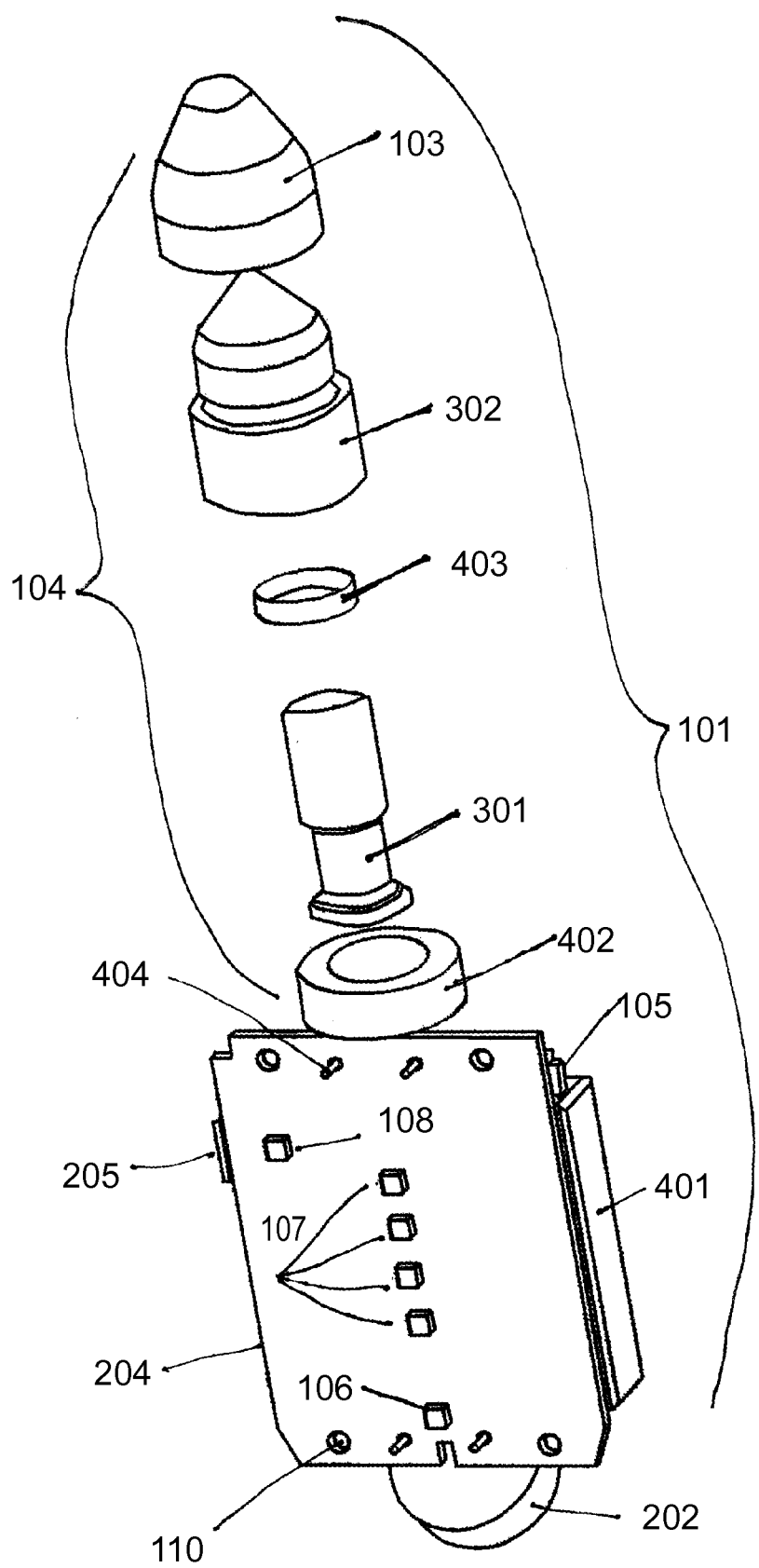
FIG. 4 is a partially exploded perspective view of the internal components of a portable diagnostic instrument according to an embodiment.

FIG. 4 is an exploded perspective view of the internal components of a portable diagnostic instrument according to an embodiment.

A control unit for the device 101 can comprise an electronic circuit board 401. Part of the electronic circuit board 401 can include a rechargeable battery (not shown). The battery can be used to power both the auditory function and the vibratory function of the device 101 and the user can control the power supply through the use of the switches for each function 105 and 204. The circuit board 401 can also control the indicator lights 106, 107 and 108, which can inform the user the charging status, the frequency output of the device 101 and the charge remaining in the battery, respectively. The circuit board 401 and indicator light 106 can also be part of a warning unit, which can indicate the power status of the device 101. The circuit board can also control the power provided to the speaker 202 and the vibratory unit 104. Specifically, the control unit can maintain the proper frequencies produced by the device auditory unit and vibratory unit 104 even when battery power is low by increasing the flow of current as the battery's potential drops. The vibratory unit 104 can be supplied power through the vibratory post 301, which can be surrounded by a cage 402 that can provide protection for the vibration generator (not pictured). A washer 403 can be placed around the vibratory post 301 and on top of the washer can be the first 302 and second 103 caps for the vibratory unit 104.

The circuit board 401 can contain screw holes 110 that screws (not pictured) can pass through to attach the circuit board 401 to the housing 102 as well as both sides of the housing together. Pins 404 can be located on the circuit board 401 to assure the correct alignment between the housing 102 and the components of the circuit board 401.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A portable diagnostic instrument comprising:
   an auditory unit capable of producing sounds at two of more frequencies;
   a vibratory unit capable of producing vibration at two or more frequencies;
   a control unit to control the auditory unit and the vibratory unit;
   the vibratory unit capable of producing a continuous vibration at a single frequency for any length of time specified by the control unit;
   the auditory unit capable of producing a continuous sound at a single frequency for any length of time specified by the control unit;
   a first cap covering the vibratory unit wherein the vibration produced by the vibratory unit is concentrated to a single point at a tip of the first cap; and
   a warning unit to monitor the instrument's power status.

2. The portable diagnostic instrument as described in claim 1 wherein the auditory unit comprises a speaker.

3. The portable diagnostic device as described in claim 2 wherein the speaker is recessed in relation to the edge of the case.

4. The portable diagnostic device as described in claim 3 wherein the speaker is protected by a bar across the front of the speaker.

5. The portable diagnostic instrument as described in claim 1 wherein the case also comprises a hole for use in attaching the device to other objects.

6. The portable diagnostic instrument as described in claim 1 wherein the vibratory unit comprises a piece for testing the Babinski reflex of a patient.

7. The portable diagnostic instrument as described in claim 1 wherein the control unit comprises lights to indicate the frequency of the output emitted from the device.

8. The portable diagnostic instrument as described in claim 1 wherein the instrument comprises a slot for the attachment of accessories.

9. The portable diagnostic instrument as described in claim 1 wherein the instrument is powered by a rechargeable battery.

10. The portable diagnostic instrument as described in claim 9 wherein the warning unit comprises a light emitting diode which can be one color when the rechargeable battery is fully charge, another when a charge is needed soon and flashes when the device should not be used and needs to be recharged.

11. The portable diagnostic instrument as described in claim 9 wherein the warning unit comprises a light emitting diode which can be one color when fully charge, another when charging and a third when the device is unable to be charged.

12. The portable diagnostic instrument as described in claim 1 wherein the control unit can maintain proper frequencies even when the power being supplied to the instrument is diminished.

13. A method for using a portable diagnostic instrument, the method comprising:
   providing a unit combining a vibratory unit, a first end cap covering the vibratory unit and an auditory unit;
   the first end cap having a point wherein the vibration produced by the vibratory unit is concentrated;
   turning on the vibratory unit to produce a continuous vibration at a single frequency;
   adjusting the frequency of the vibratory unit;
   placing the point of the first end cap of the vibratory unit into contact with a patient and observing the reaction produced by the contact;
   turning off the vibratory unit;
   turning on the auditory unit to produce sound;
   varying the frequency of the sound produced by the device; and
   observing which frequencies are perceptible by the patient.

* * * * *